United States Patent
Ostergard

(10) Patent No.: US 8,657,773 B2
(45) Date of Patent: Feb. 25, 2014

(54) ANKLE BRACE

(76) Inventor: Doak Ostergard, Lincoln, NE (US)

( * ) Notice: Subject to any disclaimer, the term of this patent is extended or adjusted under 35 U.S.C. 154(b) by 336 days.

(21) Appl. No.: 13/134,087

(22) Filed: May 27, 2011

(65) Prior Publication Data

US 2012/0302933 A1    Nov. 29, 2012

(51) Int. Cl.
*A61F 5/00* (2006.01)
*A43B 7/14* (2006.01)
*A43B 7/20* (2006.01)

(52) U.S. Cl.
USPC .................. 602/27; 602/23; 36/88; 36/89

(58) Field of Classification Search
USPC ........... 602/27, 23, 5, 28; 128/882; 36/88, 89, 36/91, 92, 140, 11.5
See application file for complete search history.

(56) References Cited

U.S. PATENT DOCUMENTS

| 2008/0082034 A1 | 4/2008 | Wilkerson |
| 2008/0306422 A1 | 12/2008 | McChesney et al. |
| 2009/0216167 A1 | 8/2009 | Harris |
| 2009/0247923 A1 | 10/2009 | Lundberg |

*Primary Examiner* — Victoria J Hicks
(74) *Attorney, Agent, or Firm* — Dennis L. Thomte; Thomte Patent Law Office LLC

(57) ABSTRACT

An ankle brace which is positioned on an ankle of a person and which incorporates a tensioning structure which permits full range of motion to the ankle joint but which prevents the ankle joint from moving past its normal range of motion to protect the ankle joint.

10 Claims, 8 Drawing Sheets

ANKLE BRACE

BACKGROUND OF THE INVENTION

1. Field of the Invention

This invention relates to an ankle brace and more particularly to an ankle brace including a tensioning system which functionally stabilizes the ankle as it reaches extreme ranges of motion.

2. Description of the Related Art

Conventional braces for protecting joints of the body do so by restricting or limiting motion to the joint to which it is applied to prevent a new injury or protect a pre-existing injury. In some cases, this may be effective but in other cases such as in athletics it is not very functional providing that their joints can function within normal ranges of motion. An ankle joint, just like all the joints in the human body, has a natural range of motion that it can move through without causing damage to itself. As it reaches the end of these ranges, the body has structure such as ligaments and tendons to create tension to end range of motion and protect the joint. Many of the prior art ankle braces do prevent the ankle exceeding its extreme ranges of motion but do not provide the necessary flexibility to permit the athlete to function normally.

SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

An ankle brace is disclosed which includes an elongated, generally flat sole or sole plate having a forward end, a medial side, a lateral side and a rearward end. The brace also includes an upstanding flexible medial connector member having an upper end, a lower end, a rearward end, a forward end, an inner surface and an outer surface with the lower end of the medial connector being hingedly connected to the medial side of the sole plate. An upstanding medial support member having an upper end, a lower end, a rearward end, a forward end, an inner surface and an outer surface is also provided with the inner surface of the medial support member being positioned adjacent the outer surface of the medial connector member. The medial support member is secured to the medial connector member with the lower end of the medial support member being positioned above the lower end of the medial connector member at the medial side of the sole plate to create a flexible hinge.

An elongated first elastic cord has one end thereof secured to the medial connector member. The brace also includes a first elongated flexible strap having one end thereof secured to the medial support member at the rearward end thereof. A second elongated flexible strap is provided with the one end of the second strap being secured to the medial support member at the forward end thereof.

An upstanding flexible lateral connector member is provided having an upper end, a lower end, a rearward end, a forward end, an inner surface and an outer surface with the flexible lateral connector member having a plurality of spaced-apart loops at the upper end thereof. The lower end of the lateral connector member is hingedly connected to the lateral side of the sole plate. An upstanding lateral support member having an upper end, a lower end, a rearward end, a forward end, an inner surface and an outer surface is positioned outwardly of the lateral connector member so that the inner surface of the lateral support member is positioned adjacent the outer surface of the lateral connector member. An elongated second elastic cord has one end thereof secured to the lateral connector member.

The ankle brace of this invention also includes a third elongated flexible strap which is adapted to be secured together to form an adjustable loop for positioning around a person's leg above the ankle brace with the loop having medial and lateral sides. A third connector is mounted on the medial side of the loop and has a plurality of spaced-apart loops at the lower end thereof. A fourth connector member is mounted on the lateral side of the loop and has a plurality of spaced-apart loops at the lower end thereof. A cord fastening device is mounted on the outer side of the medial support member and a cord fastening device is mounted on the outer side of the lateral support member. The first cord interconnects the loops of the third connector member and the medial connector member with the second cord being threaded through the loops of the fourth connector member and the medial connector member to form a tensioning system that functionally stabilizes the ankle as it reaches its extreme range of motion but which permits the ankle to function between its extreme ranges of motion.

It is therefore a principal object of the invention to provide an improved ankle brace.

A further object of the invention is to provide an ankle brace including a tensioning system which limits the end range of ankle motions and protects the ankle joint.

A further object of the invention is to provide an ankle brace which does not interfere with the functional motions of the ankle between its end range of motion.

A further object of the invention is to provide an ankle brace which includes hinged portions at the medial and lateral sides of a sole plate to ensure that the sole of the brace stays in contact with the sole of the foot.

Yet another object of the invention to provide an adjustable tensioning system for the ankle brace of this invention.

Yet another object of the invention is to provide an ankle brace which may also be incorporated into a shoe.

These and other objects will be apparent to those skilled in the art.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DESCRIPTION OF THE PREFERRED EMBODIMENT

Figure 1:
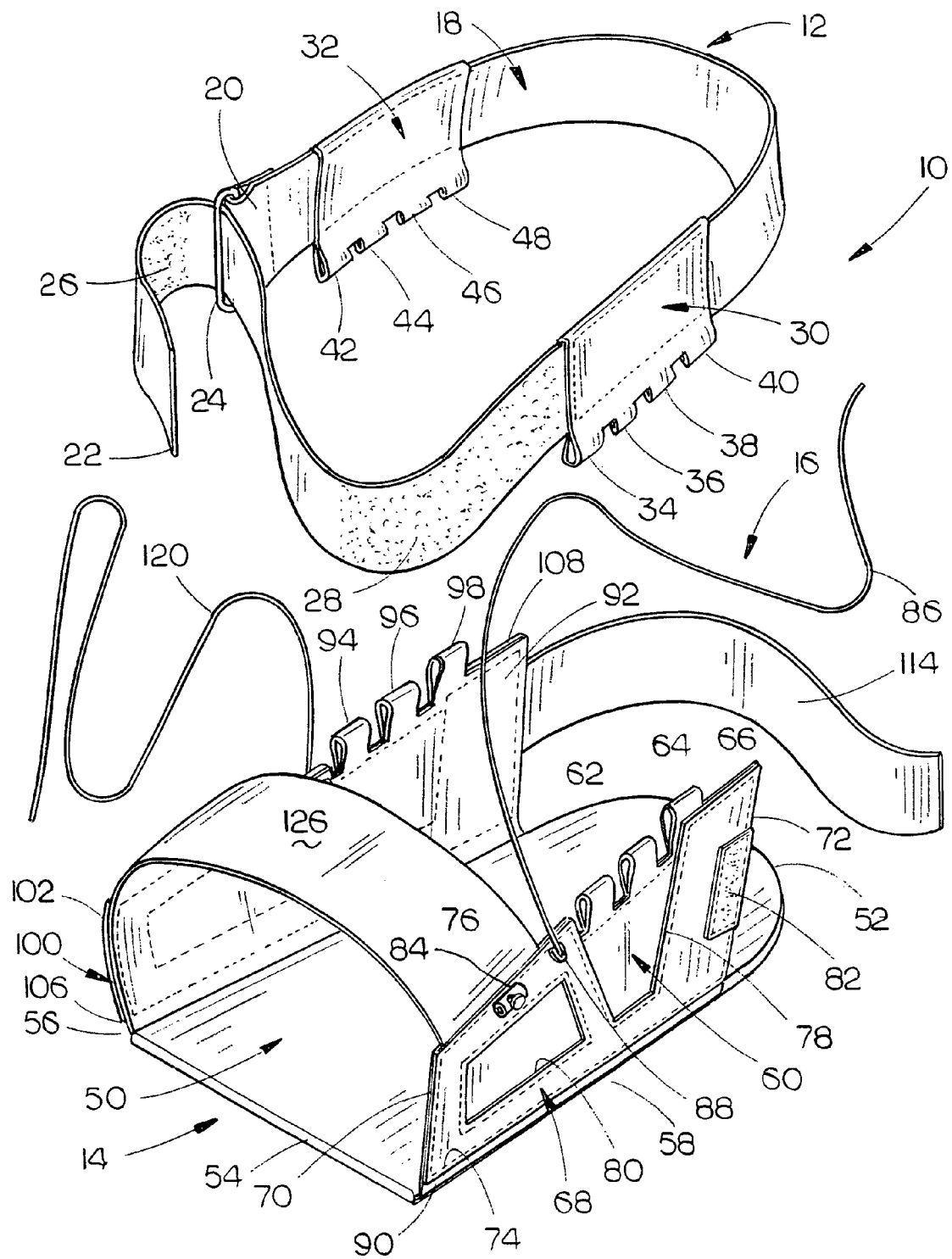
FIG. 1 is an exploded perspective view of the ankle brace of this invention.

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense in that the scope of the present invention is defined only by the appended claims.

The ankle brace of this invention is referred to generally by the reference numeral 10. Brace 10 is comprised of three key components, namely a strap assembly 12, foot portion 14 and a tensioning system 16.

Strap assembly 12 includes a 1½ inch to 2 inch flexible strap 18 having ends 20 and 22. Ring 24 is secured to end 20 of strap 18 as seen in FIG. 1. A strip of loop fasteners 26 is secured to the outer surface of strap 18 at end 22. A strip of hook fasteners 28 is also secured to the outer surface of strap 18. Together, the loop and hook fasteners form a VELCRO® connection system. Connector members 30 and 32 are secured to strap 18 by stitching or the like. Connector member 30 has spaced-apart loops or eyes 34, 36, 38 and 40 at its lower end (FIG. 1). Connector member 32 has spaced-apart loops or eyes 42, 44, 46 and 48 at its lower end (FIG. 1).

Foot portion 14 includes a sole 50 having an arcuate rearward end 52 and a forward end 54. Sole 50 has a low profile and preferably extends approximately two-thirds of the way from the heel towards the toes of the person wearing the ankle brace 10. Sole 50 is constructed of semi-rigid material and will act as a lever arm to create tension in the tension system. For purposes of description, sole 50 will be described as having a medial side 56 and a lateral side 58.

A flexible connector member 60 has its lower end secured to sole 50 at the lateral side 58 thereof by any convenient means such as by stitching. The upper end of connector member 60 has spaced-apart loops or eyes 62, 64 and 66. The numeral 68 refers to a support member constructed of a semi-rigid material such as plastic or the like. Support member 68 will be described as having a forward end 70, rearward end 72, lower end 74 and upper end 76. Support member 68 has a notch 78 formed therein which extends downwardly thereinto from the upper end thereof. Support member 68 also has an opening 80 formed therein. Support member 68 has a strip of loop fasteners 82 secured thereto at the rearward end thereof. A tubular locking device 84 of conventional design is secured to support member 68 as seen in FIG. 1. One end of an elastic cord 86 is secured to support member 68 at 88. Support member 68 is secured to the outer side of connector member 60 by stitching or the like so that its lower end 74 is spaced above sole 50 to create a flexible hinge channel 90 which runs parallel to the sole 50 on the lateral side 58 thereof to create a natural hinge and adjustability for width. The hinge channel 90 creates a break to ensure that the sole 50 of the brace 10 stays in contact with the sole of the foot.

A flexible connector member 92 has its lower end secured to sole 50 at the medial side 56 thereof by any convenient means such as by stitching. The upper end of connector member 92 has spaced-apart loops or eyes 94, 96 and 98. The numeral 100 refers to a support member constructed of a semi-rigid material such as plastic or the like. Support member 100 will be described as having a forward end 102, rearward end 104, lower end 106 and upper end 108. Support member 100 has a notch 110 formed therein which extends downwardly thereinto from the upper end thereof. Support member 100 also has an opening 112 formed therein. Support member 100 has a strap 114 secured thereto at the rearward end thereof by stitching or the like. The free end of strap 114 has a plurality of hook fasteners 116. A tubular locking device 118 of conventional design is secured to support member 100 as seen in FIG. 1. One end of an elastic cord 120 is secured to support member 100 at 122. Support member 100 is secured to the outer side of connector member 92 by stitching or the like so that its lower end 106 is spaced above sole 50 and to the lower end of connector member 100 to create a flexible hinge channel 124 which runs parallel to the sole 50 on the medial side 56 thereof to create a natural hinge and adjustability for width. The hinge channel 124 creates a break to ensure that the sole 50 of the brace 10 stays in contact with the sole of the foot. A flexible strap 126 has one end thereof secured to the upper forward end of connector member 60 and its other end secured to the upper forward end of connector member 92.

Figure 2:
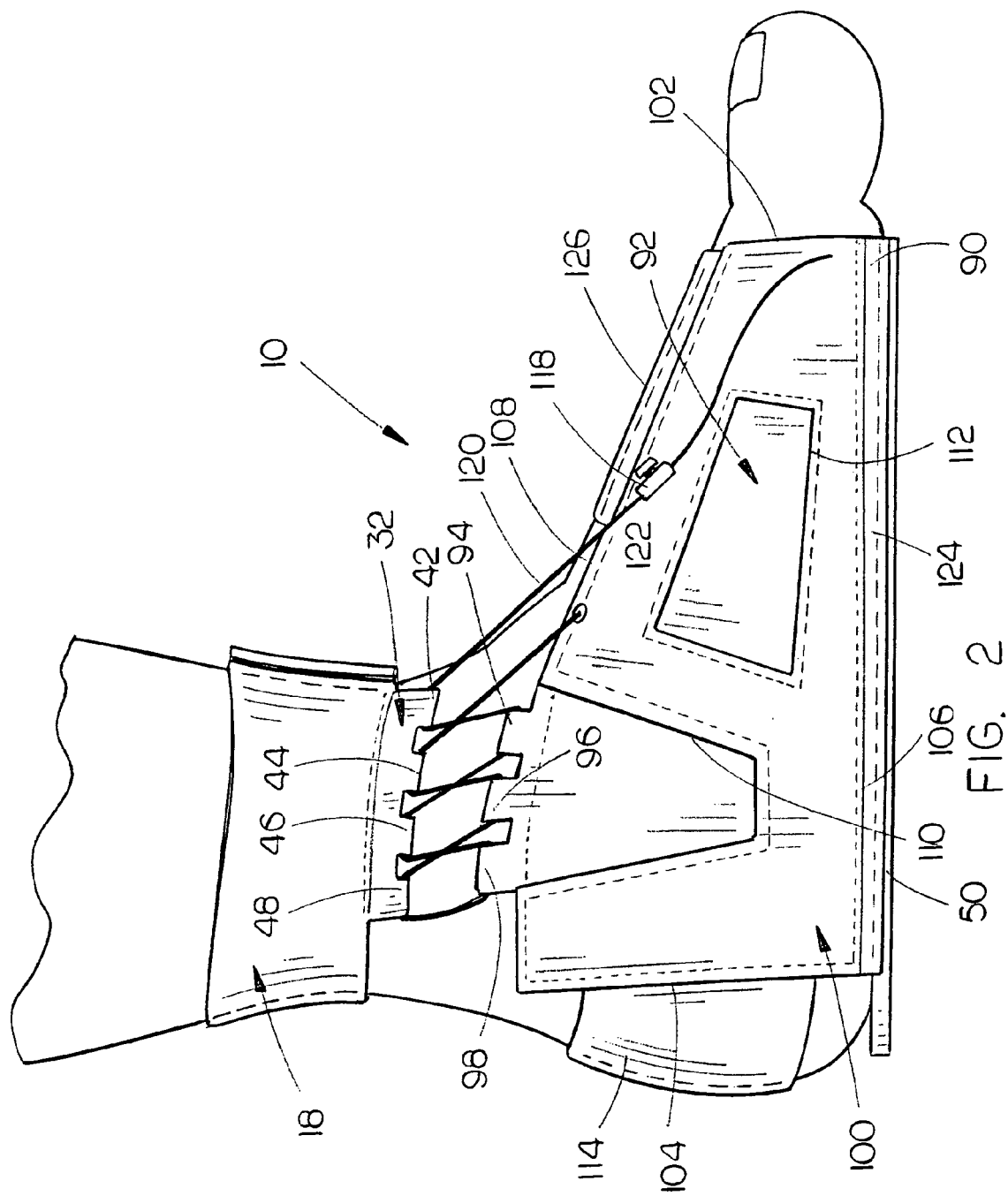
FIG. 2 is a side view of the brace of FIG. 1 secured to the left foot and ankle of a person.
Figure 3:
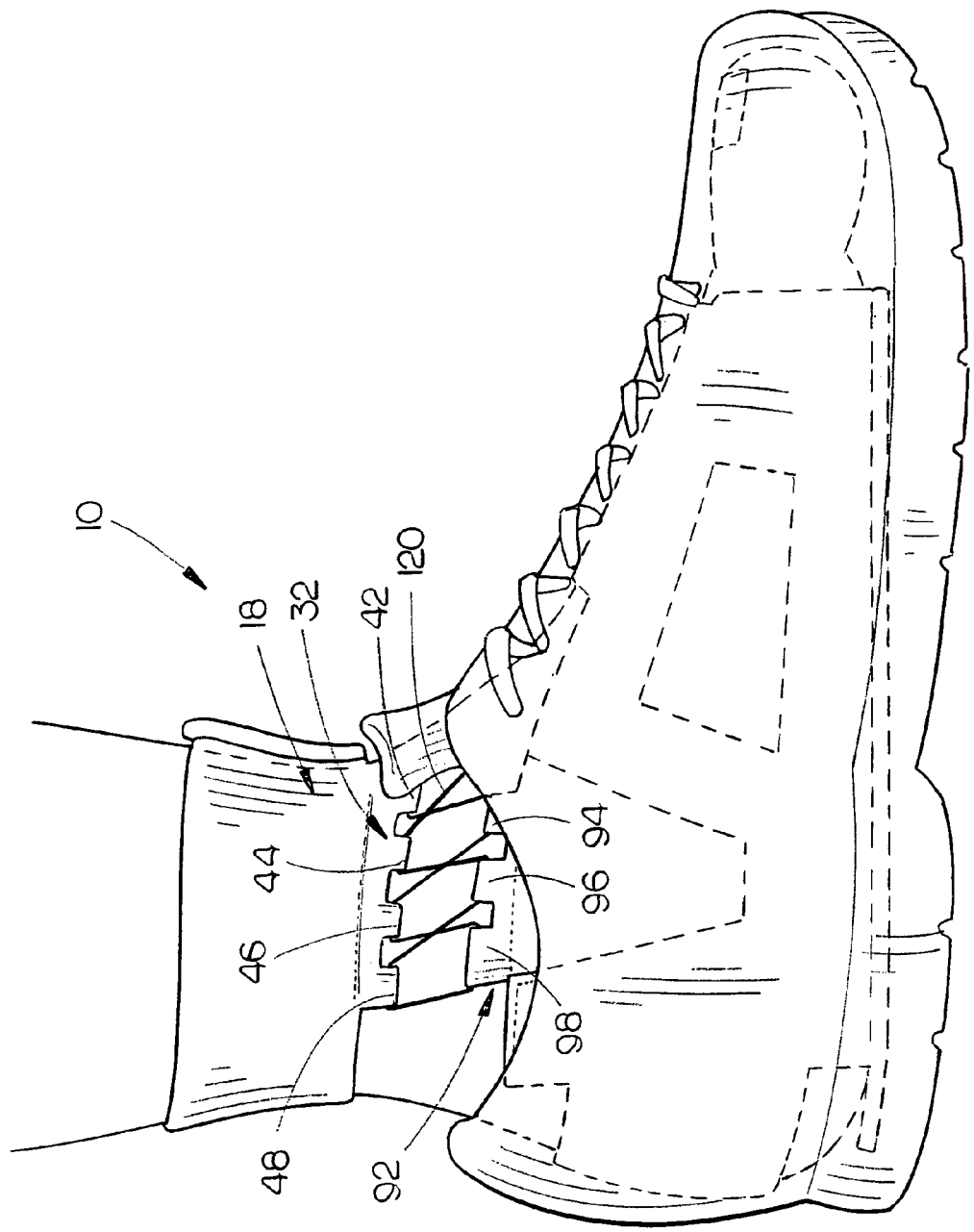
FIG. 3 is a side elevational view illustrating the person's foot and ankle brace inserted into a shoe.

FIG. 2 illustrates one method of threading or lacing the tension cord 120 to and between the connector members 32 and 92. Cord 120 is extended upwardly and rearwardly from 122, thence rearwardly through loop 44, thence downwardly, thence rearwardly through loop 96, thence upwardly and rearwardly, thence rearwardly through loop 48, thence downwardly, thence forwardly through loop 98, thence upwardly, thence forwardly through loop 46, thence downwardly and forwardly, thence forwardly through loop 94; thence upwardly, thence forwardly through loop 42, and thence downwardly and forwardly, and thence through the tubular locking device 118. The tension in the cord 120 is easily adjusted through the use of the locking device 118. The cord 86 on the lateral side of the ankle brace 10 may be similarly laced or threaded to connect the connector members 30 and 60.

Figure 4:
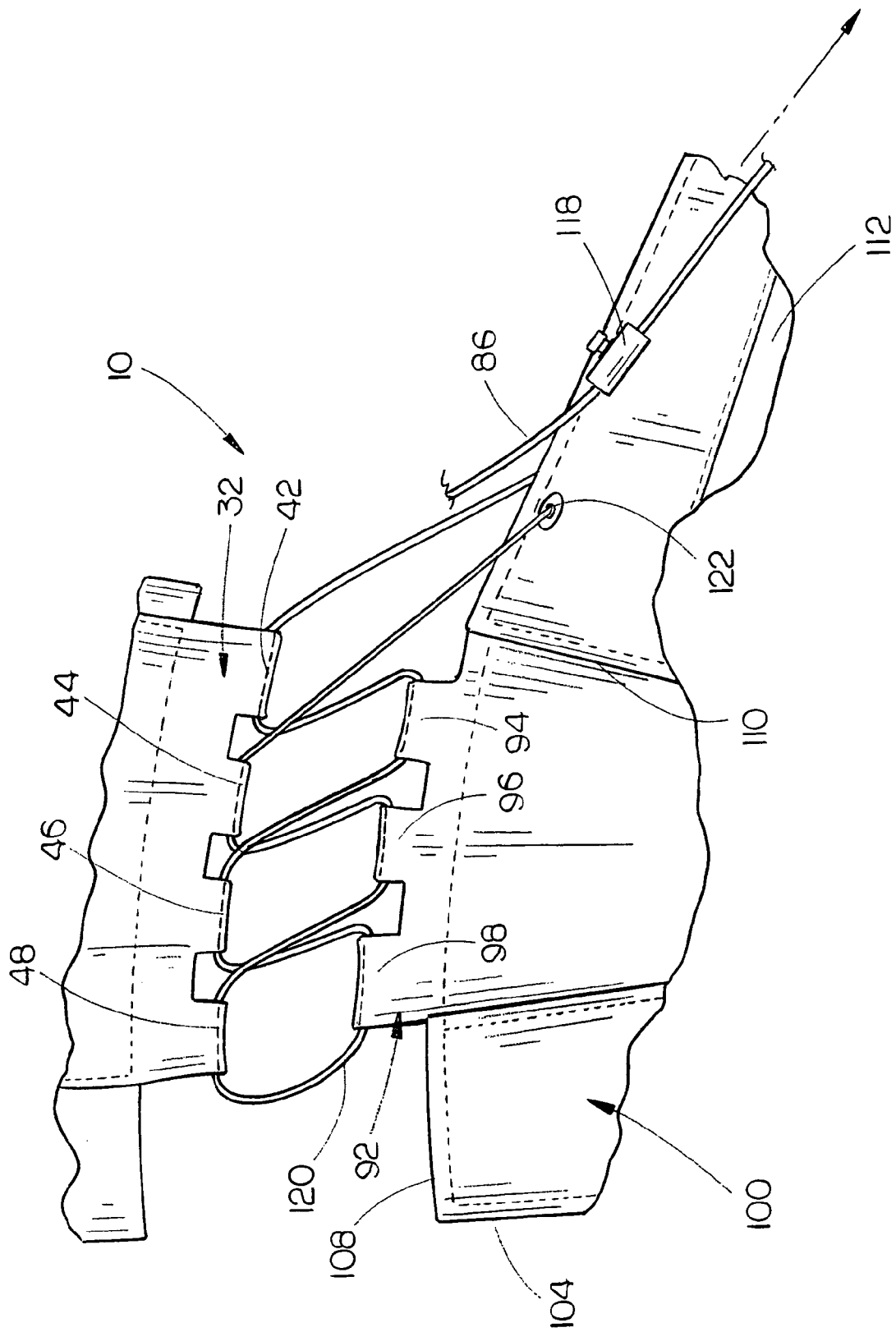
FIG. 4 is a partial side view of the ankle brace illustrating one method of threading or lacing the tension cords of the invention.
Figure 7:
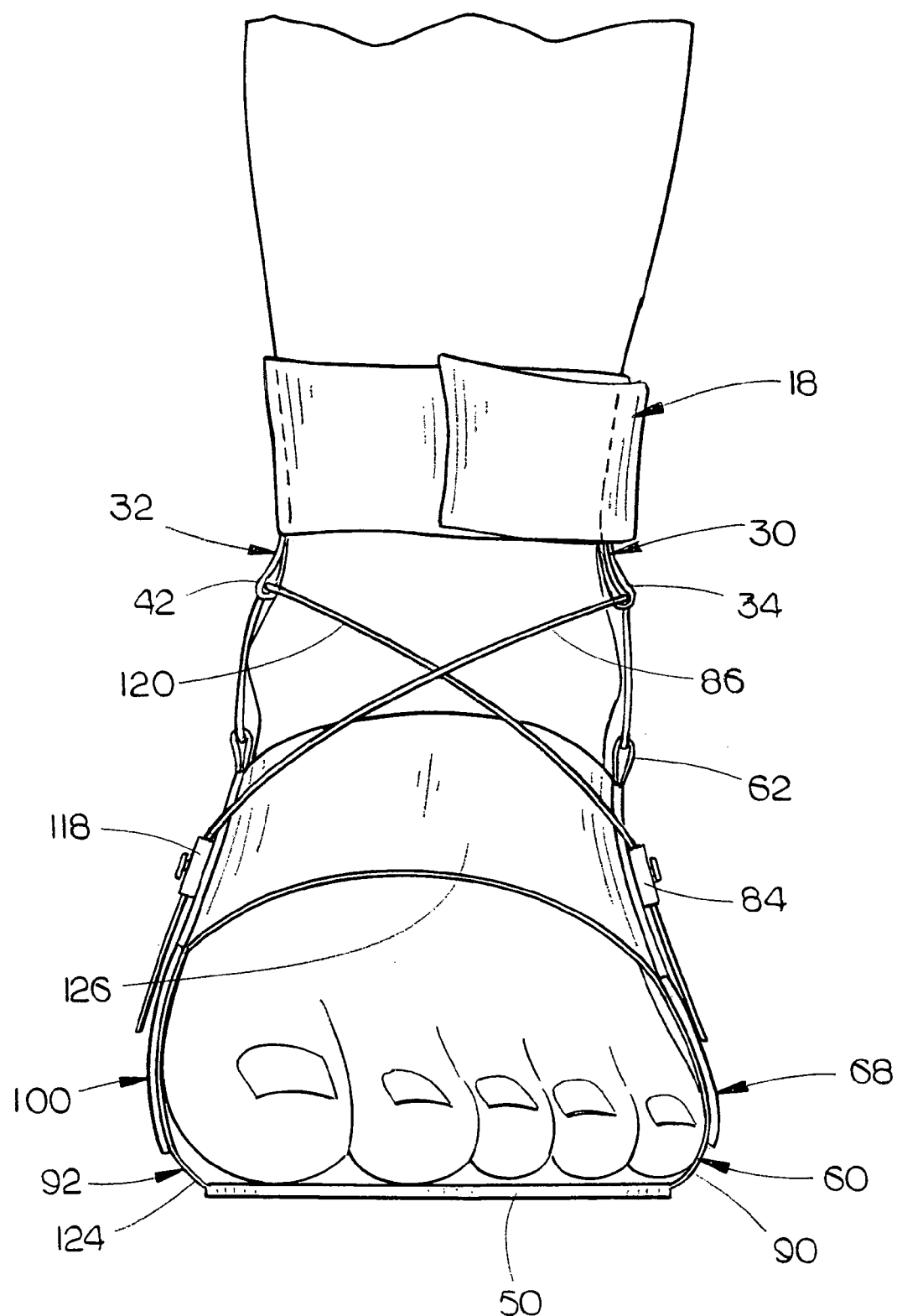
FIG. 7 is a front view of the ankle brace illustrating the FIG. 4 method of threading or lacing the tensioning cords of the invention.
Figure 8:
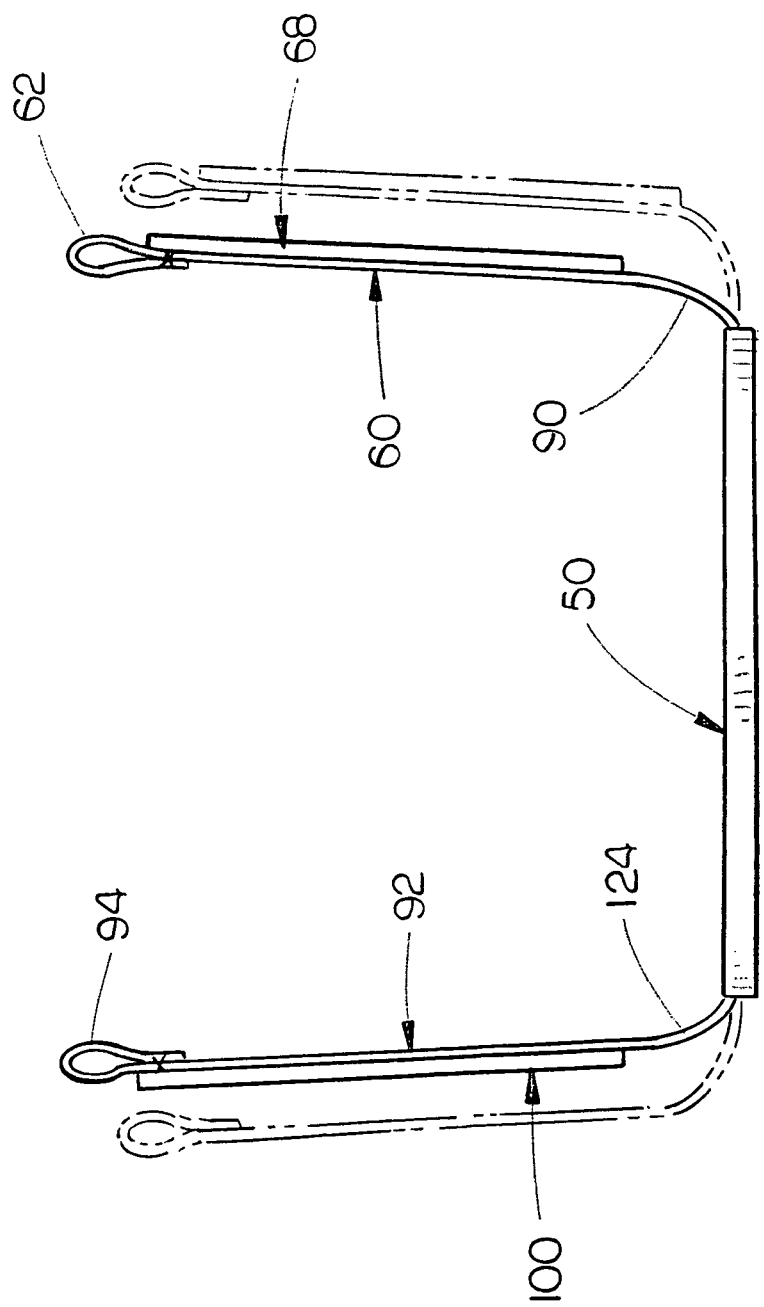
FIG. 8 is a partial front view illustrating the manner in which the width of the ankle brace may be changed due to the hinges at either side of the sole plate of the invention.

FIG. 4 illustrates another method of threading or lacing the connector members 32 and 92 together by the cord 120. Cord 120 is extended upwardly and rearwardly from 122, thence rearwardly through loop 44, thence downwardly, thence rearwardly through loop 96, thence upwardly and rearwardly, thence rearwardly through loop 48, thence downwardly, thence forwardly through loop 98, thence upwardly, thence forwardly through loop 46, thence downwardly and forwardly, thence forwardly through loop 94, thence upwardly, and thence forwardly through loop 42. The free end of cord 120 may then be inserted through locking device 118 or through the locking device 84 on support member 68 at the lateral side of the brace 10 as seen in FIG. 7. The cord 86 is similarly laced or threaded between connector members 30 and 60 with cord 86 being received by locking device 118 on support member 100.

Figure 5:
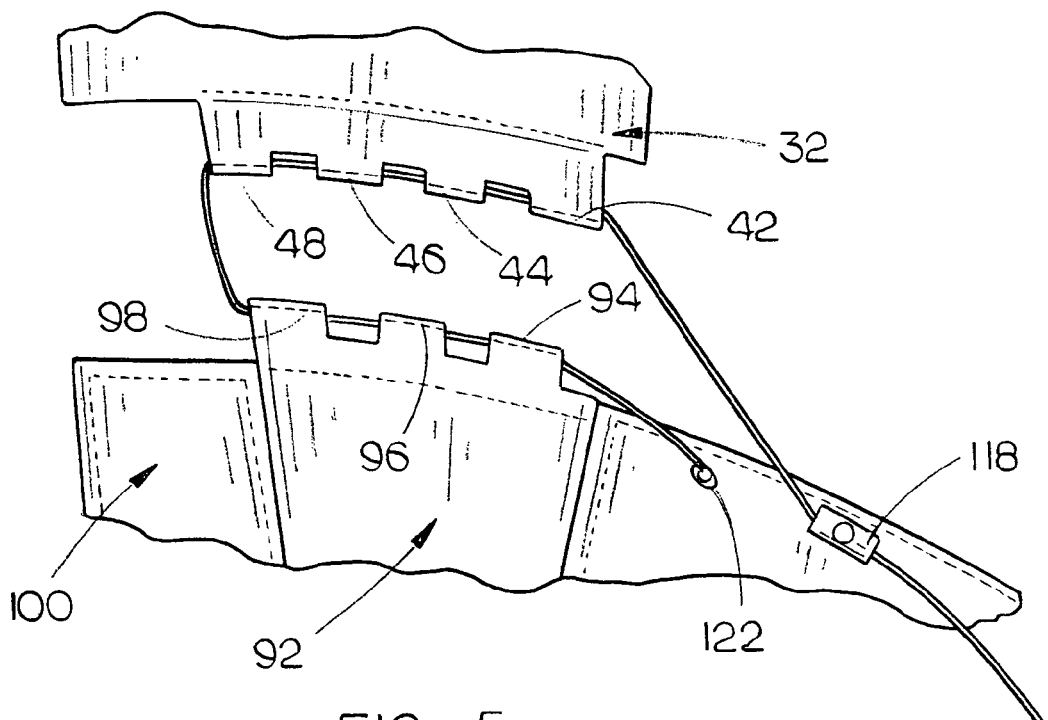
FIG. 5 is a partial side view of the ankle brace illustrating another method of threading or lacing the tensioning cords of the invention.
Figure 6:
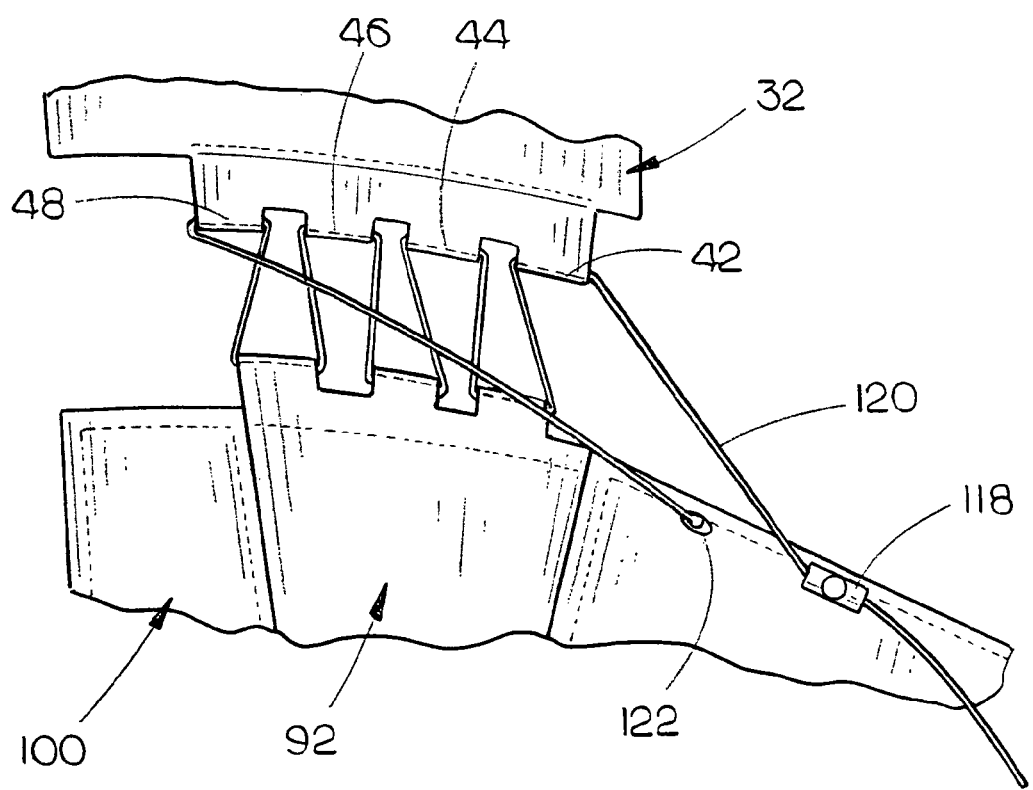
FIG. 6 is a partial side view of the ankle brace illustrating yet another method of threading or lacing the tensioning cords of the invention.

FIGS. 5 and 6 illustrate further methods of lacing or threading connector members 32 and 92 together. The connector members 30 and 60 at the lateral side of the brace would be connected in the same manner as that shown in FIGS. 5 and 6.

Figure 9:
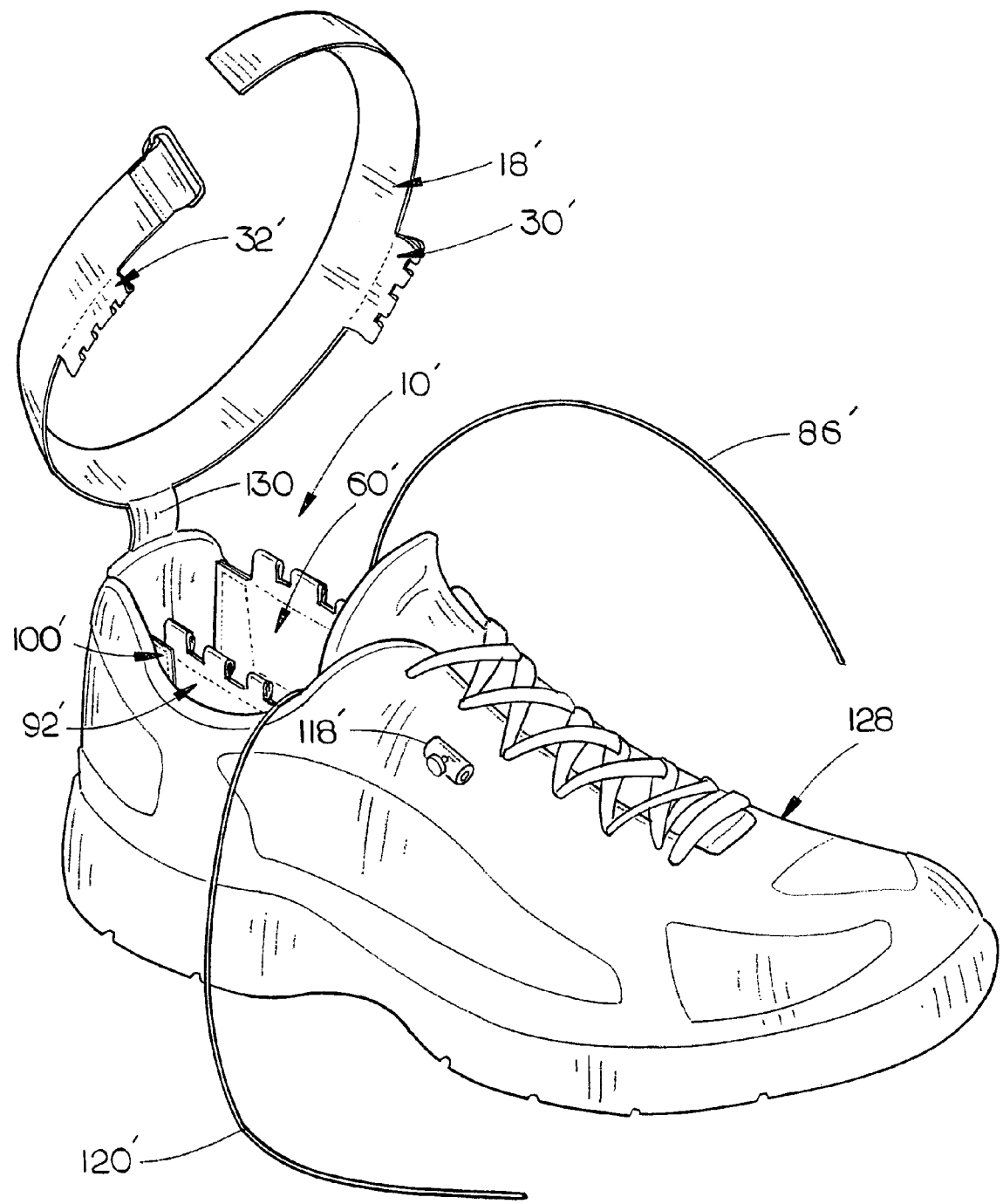
FIG. 9 is a partial perspective view illustrating a second embodiment of the ankle brace wherein the ankle brace is incorporated into a shoe.

FIG. 9 illustrates a modified form of the ankle brace of this invention. In FIG. 9, the ankle brace 10' is incorporated into a shoe 128. The sole of the ankle brace 10' may be the sole of the shoe or may be a sole glued or otherwise secured to the shoe

128. As seen in FIG. 9, the locking device 118' is secured to the shoe 128 rather than the support member 100'. The designation "'" is used on the ankle brake 10' in FIG. 9 to refer to similar components of the ankle brace 10.

In use, the elastic cord 86 which interconnects the connector member 30 and 60 and the elastic cord 120 which interconnects the connector members 32 and 92 permit the person wearing the ankle brace 10 to have normal fore to aft and lateral to medial movement. The cords 86 and 120 permit a certain amount of movement of the ankle but when the ankle reaches its outer ranges of movement, the elastic cords 86 and 120 resist further movement of the ankle. In other words, the ankle brace of this invention permits the ankle to move within the natural range of motion but when the ankle reaches the end of those ranges, the cords 86 and 120 create tension to end the range of motion to protect the ankle joint.

Although the invention has been described in language that is specific to certain structures and methodological steps, it is to be understood that the invention defined in the appended claims is not necessarily limited to the specific structures and/or steps described. Rather, the specific aspects and steps are described as forms of implementing the claimed invention. Since many embodiments of the invention can be practiced without departing from the spirit and scope of the invention, the invention resides in the claims hereinafter appended.

I claim:

1. An ankle brace for use with a shoe, comprising:
    an elongated, generally flat sole plate positioned in the shoe and having a forward end, a rearward end, a medial side and a lateral side;
    an upstanding flexible medial connector member having an upper end, a lower end, a rearward end, a forward end, an inner surface and an outer surface;
    said upstanding flexible medial connector member having a plurality of spaced-apart loops at said upper end thereof;
    said lower end of said upstanding flexible medial connector member being connected to said sole plate at said medial side of said sole plate;
    an elongated first elastic cord having first and second ends;
    said first end of said elongated first elastic cord being operatively secured to said upstanding flexible medial connector member;
    an upstanding flexible lateral connector member having an upper end, a lower end, a rearward end, a forward end, an inner surface and an outer surface;
    said upstanding flexible lateral connector member having a plurality of spaced-apart loops at said upper end thereof;
    said lower end of said upstanding flexible lateral connector member being connected to said lateral side of said sole plate;
    an elongated second elastic cord having first and second ends;
    said first end of said elongated second elastic cord being operatively secured to said upstanding flexible lateral connector member;
    a first elongated flexible strap having first and second ends;
    a means associated with said first elongated flexible strap so as to form an adjustable loop for positioning around a person's leg with the adjustable loop having medial and lateral sides;
    a third connector member mounted on said medial side of said adjustable loop;
    said third connector member having a lower end which has a plurality of spaced-apart loops thereon;
    a fourth connector member mounted on said lateral side of said adjustable loop;
    said fourth connector member having a lower end which has a plurality of spaced-apart loops thereon;
    a first cord fastening device operatively secured to the shoe;
    a second cord fastening device operatively secured to the shoe;
    said elongated first elastic cord interconnecting said plurality of spaced-apart loops on said upstanding flexible medial connector member and said plurality of spaced-apart loops on said third connector member with the second end of said elongated first elastic cord being length adjustably secured to one of said first and second cord fastening devices;
    said elongated second elastic cord interconnecting said plurality of spaced-apart loops on said upstanding flexible lateral connector member with said plurality of spaced-apart loops on said fourth connector member with the second end of said elongated second elastic cord being length adjustably secured to the other of said first and second cord fastening devices.

2. The ankle brace of claim 1 wherein said sole plate is constructed of a semi-rigid material.

3. The ankle brace of claim 1 wherein said upstanding flexible medial connector member, said upstanding flexible lateral connector member, said third connector member and said fourth connector member are flexible.

4. The ankle brace of claim 1 wherein each of said upstanding flexible medial connector member and said upstanding flexible lateral connector members is constructed of a flexible material.

5. The ankle brace of claim 1 wherein a medial support member is secured to said upstanding flexible medial connector member at the outer surface of said upstanding flexible medial connector member thereof and wherein a lateral support member is secured to said upstanding flexible lateral connector member at said outer surface of said upstanding flexible lateral connector member.

6. An ankle brace for use with a shoe having a sole with a forward end, a rearward end, a medial side and a lateral side, comprising:
    an upstanding flexible medial connector member having an upper end, a lower end, a rearward end, a forward end, an inner surface and an outer surface;
    said upstanding flexible medial connector member having a plurality of spaced-apart loops at said upper end thereof;
    said lower end of said upstanding flexible medial connector member being connected to the sole at the medial side of the sole;
    an elongated first elastic cord having first and second ends;
    said first end of said elongated first elastic cord being operatively secured to said upstanding flexible medial connector member;
    an upstanding flexible lateral connector member having an upper end, a lower end, a rearward end, a forward end, an inner surface and an outer surface;
    said upstanding flexible lateral connector member having a plurality of spaced-apart loops at said upper end thereof;
    said lower end of said upstanding flexible lateral connector member being connected to the lateral side of the sole;
    an elongated second elastic cord having first and second ends;
    said first end of said elongated second elastic cord being operatively secured to said upstanding flexible lateral connector member;
    a first elongated flexible strap having first and second ends;

a means associated with said first elongated flexible strap so as to form an adjustable loop for positioning around a person's leg with the loop having medial and lateral sides;

a third connector member mounted on said medial side of said adjustable loop;

said third connector member having a lower end which has a plurality of spaced-apart loops thereon;

a fourth connector member mounted on said lateral side of said adjustable loop;

said fourth connector member having a lower end which has a plurality of spaced-apart loops thereon;

a first cord fastening device operatively secured to the shoe;

a second cord fastening device operatively secured to the shoe;

said elongated first elastic cord interconnecting said plurality of spaced-apart loops on said upstanding flexible medial connector member and said plurality of spaced-apart loops on said third connector member with the second end of said elongated first elastic cord being length adjustably secured to one of said first and second cord fastening devices;

said elongated second elastic cord interconnecting said plurality of spaced-apart loops on said upstanding flexible lateral connector member with said plurality of spaced-apart loops on said fourth connector member with the second end of said elongated second elastic cord being length adjustably secured to the other of said first and second cord fastening devices.

7. The ankle brace of claim 6 wherein the sole is constructed of a semi-rigid material.

8. The ankle brace of claim 6 wherein said upstanding flexible medial connector member, said upstanding flexible lateral connector member, said third connector member and said fourth connector member are flexible.

9. The ankle brace of claim 6 wherein said upstanding flexible medial connector member and said upstanding flexible lateral connector members are constructed of a flexible material.

10. The ankle brace of claim 6 wherein a medial support member is secured to said upstanding flexible medial connector member at the outer surface of said upstanding flexible medial connector member and wherein a lateral support member is secured to said upstanding flexible lateral connector member at said outer surface of said upstanding flexible lateral connector member.

\* \* \* \* \*